US011572467B2

(12) United States Patent
Nakai et al.

(10) Patent No.: US 11,572,467 B2
(45) Date of Patent: Feb. 7, 2023

(54) RESIN COMPOSITION FOR ACOUSTIC MATCHING LAYER, CURED PRODUCT, ACOUSTIC MATCHING SHEET, ACOUSTIC PROBE, ACOUSTIC MEASURING APPARATUS, METHOD FOR PRODUCING ACOUSTIC PROBE, AND ACOUSTIC MATCHING LAYER MATERIAL SET

(71) Applicant: FUJIFILM Corporation, Tokyo (JP)

(72) Inventors: Yoshihiro Nakai, Kanagawa (JP); Kazuhiro Hamada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 357 days.

(21) Appl. No.: 16/863,365

(22) Filed: Apr. 30, 2020

(65) Prior Publication Data

US 2020/0255653 A1  Aug. 13, 2020

Related U.S. Application Data (63) Continuation of application No. PCT/JP2018/040439, filed on Oct. 31, 2018.

(30) Foreign Application Priority Data

Nov. 1, 2017  (JP) ............... JP2017-212210

(51) Int. Cl.
| | | |
|---|---|---|
| G01N 29/24 | (2006.01) | |
| G10K 11/36 | (2006.01) | |
| C08G 59/24 | (2006.01) | |
| C08G 59/32 | (2006.01) | |
| C08G 59/66 | (2006.01) | |
| C08L 63/04 | (2006.01) | |
| C08G 59/06 | (2006.01) | |
| C08L 63/02 | (2006.01) | |
| C08K 3/011 | (2018.01) | |
| C08K 3/08 | (2006.01) | |
| C08K 5/37 | (2006.01) | |

(52) U.S. Cl.
CPC .............. *C08L 63/04* (2013.01); *C08G 59/06* (2013.01); *C08G 59/245* (2013.01); *G01N 29/2437* (2013.01); *G10K 11/36* (2013.01); *C08K 3/011* (2018.01); *C08K 3/08* (2013.01); *C08K 5/37* (2013.01)

(58) Field of Classification Search
None
See application file for complete search history.

(56) References Cited

U.S. PATENT DOCUMENTS

| | | | |
|---|---|---|---|
| 5,430,112 A | 7/1995 | Sakata et al. | |
| 2008/0098816 A1 | 5/2008 | Yamashita et al. | |
| 2009/0032293 A1 | 2/2009 | Miyakawa et al. | |
| 2010/0273940 A1* | 10/2010 | Urakawa ............... | C08G 59/66 560/147 |
| 2012/0077903 A1* | 3/2012 | Yamagami ............ | C09D 7/20 523/400 |
| 2016/0338666 A1 | 11/2016 | Morita | |

FOREIGN PATENT DOCUMENTS

| | | |
|---|---|---|
| EP | 1 291 390 A1 | 3/2003 |
| JP | 59-049748 A | 3/1984 |
| JP | 6-211969 A | 8/1994 |
| JP | 11-106483 A | 4/1999 |
| JP | 2004-363746 A | 12/2004 |
| JP | 2008-118212 A | 5/2008 |
| JP | 2009-267528 A | 11/2009 |
| JP | 2015-082764 A | 4/2015 |
| JP | 2015-188121 A | 10/2015 |
| JP | 2017-82124 A | 5/2017 |
| WO | 2018/066368 A1 | 4/2018 |
| WO | 2018/151993 A1 | 8/2018 |

OTHER PUBLICATIONS

International Search Report dated Jan. 15, 2019 in International Application No. PCT/JP2018/040439.
International Preliminary Report on Patentability dated Feb. 26, 2020 in International Application No. PCT/JP2018/040439.
Office Action dated Mar. 9, 2021 in Japanese Application No. 2019-550439.
Communication dated Dec. 4, 2020, from the European Patent Office in European Application No. 18872413.2.

* cited by examiner

*Primary Examiner* — Michael J Feely
(74) *Attorney, Agent, or Firm* — Sughrue Mion, PLLC (57) ABSTRACT

Provided is a resin composition for an acoustic matching layer, the resin composition including metal particles (A), an epoxy resin (B), a polythiol compound (C), and a cure-accelerating compound (D). The epoxy resin (B) includes at least one epoxy resin selected from the group consisting of bisphenol A epoxy resins, bisphenol F epoxy resins, and phenol novolac epoxy resins, and the polythiol compound (C) includes a compound having at least two specific partial structures. Also provided are a cured product formed of the composition, an acoustic matching sheet, an acoustic probe, an acoustic measuring apparatus, and a method for producing an acoustic probe. Further provided is an acoustic matching layer material set suitable for preparation of the composition.

12 Claims, 1 Drawing Sheet

RESIN COMPOSITION FOR ACOUSTIC MATCHING LAYER, CURED PRODUCT, ACOUSTIC MATCHING SHEET, ACOUSTIC PROBE, ACOUSTIC MEASURING APPARATUS, METHOD FOR PRODUCING ACOUSTIC PROBE, AND ACOUSTIC MATCHING LAYER MATERIAL SET

CROSS-REFERENCE TO RELATED APPLICATIONS

This application is a Continuation of PCT International Application No. PCT/JP2018/040439 filed on Oct. 31, 2018, which claims priority under 35 U.S.C. § 119 (a) to Japanese Patent Application No. 2017-212210 filed in Japan on Nov. 1, 2017. Each of the above applications is hereby expressly incorporated by reference, in its entirety, into the present application.

BACKGROUND OF THE INVENTION

1. Field of the Invention

The present invention relates to a resin composition for an acoustic matching layer, a cured product, an acoustic matching sheet, an acoustic probe, an acoustic measuring apparatus, a method for producing an acoustic probe, and an acoustic matching layer material set.

2. Description of the Related Art

An acoustic measuring apparatus includes an acoustic probe that irradiates a subject such as a living body with acoustic waves and receives reflected waves (echoes) therefrom to output a signal. The reflected waves received by the acoustic probe are converted into an electrical signal. The electrical signal is displayed as an image. Therefore, using an acoustic probe allows the inside of a subject to be visualized and observed.

Appropriate acoustic waves such as ultrasonic waves or photoacoustic waves are selected depending on the subject and the measurement conditions.

For example, an ultrasound diagnostic apparatus, which is an acoustic measuring apparatus, transmits ultrasonic waves toward the inside of a subject, receives ultrasonic waves reflected by a tissue inside the subject, and displays an image.

A photoacoustic measuring apparatus receives acoustic waves radiated from inside a subject due to a photoacoustic effect and displays an image. The photoacoustic effect is a phenomenon in which, when a subject is irradiated with pulses of electromagnetic waves such as visible light, near-infrared light, or microwaves, the subject absorbs the electromagnetic waves to cause heat generation and thermal expansion, whereby acoustic waves (typically, ultrasonic waves) are generated.

Since the acoustic measuring apparatus transmits and receives acoustic waves to and from a subject, the acoustic probe is required to provide acoustic impedance matching to a subject. To meet this requirement, the acoustic probe includes an acoustic matching layer. This will be described with reference to an ultrasound diagnostic apparatus search unit (also referred to as an ultrasound probe), which is an acoustic probe.

The ultrasound probe includes a piezoelectric element for transmitting and receiving ultrasonic waves and an acoustic lens configured to be in contact with a living body, and an acoustic matching layer is disposed between the piezoelectric element and the acoustic lens. Ultrasonic waves oscillated from the piezoelectric element pass through the acoustic matching layer and further through the acoustic lens to enter a living body. In general, there is a difference in acoustic impedance (density×sound velocity) between the acoustic lens and a living body. When this difference is large, ultrasonic waves are likely to be reflected by a living body surface, and the efficiency of entrance of ultrasonic waves into a living body is low. Thus, the acoustic lens is required to have acoustic impedance characteristics close to those of a living body.

On the other hand, the difference in acoustic impedance between the piezoelectric element and a living body is generally large. Accordingly, the difference in acoustic impedance between the piezoelectric element and the acoustic lens is generally large. Therefore, when the piezoelectric element and the acoustic lens are stacked on top of each other, ultrasonic waves emitted from the piezoelectric element are reflected by a surface of the acoustic lens, and the efficiency of entrance of ultrasonic waves into a living body is low. To reduce such reflection of ultrasonic waves, the above acoustic matching layer is disposed between the piezoelectric element and the acoustic lens. The acoustic impedance of the acoustic matching layer is between the acoustic impedance of a living body or the acoustic lens and the acoustic impedance of the piezoelectric element, which increases the efficiency of propagation of ultrasonic waves from the piezoelectric element to a living body. It is also known that when the acoustic matching layer has a multi-layer structure with a gradient in acoustic impedance from the piezoelectric element side toward the acoustic lens side, the efficiency of propagation of ultrasonic waves is further increased.

One example of the above acoustic matching layer is an acoustic matching layer including an amorphous carbon and particles that have a density higher than that of the amorphous carbon and are uniformly dispersed in the amorphous carbon (JP2015-082764A).

SUMMARY OF THE INVENTION

The acoustic probe is required to have sufficient mechanical strength in addition to the acoustic characteristics described above. That is, the acoustic probe is used while being rubbed, sometimes pressed, against a living body, and thus the mechanical strength directly affects the product life of the acoustic probe. Referring to the acoustic matching layer, particularly when the acoustic matching layer has a multilayer structure as described above, the thickness of each layer is required to be as thin as hundred to several hundred micrometers. In this case, the material forming the acoustic matching layer is required to be resistant to cracking if formed into a thin film, for example, by cutting processing.

With the recent increase in demand for medical equipment, high productivity has been required. For example, a composition for forming an acoustic matching layer, which is a component of an acoustic probe, has been required to have a long working life for higher handleability and to behave, after the start of curing reaction, in such a manner that it is relatively quickly cured even under mild conditions from the viewpoint of, for example, prevention of degradation and reduction of production cost.

However, the acoustic matching layer disclosed in JP2015-082764A is formed through a process in which a resin composition for an acoustic matching layer is exposed to a high temperature for a long time period (e.g., 1000° C. for 3 hours).

Thus, an object of the present invention is to provide a resin composition for an acoustic matching layer and an acoustic matching layer material set suitable for preparation of the composition. The resin composition is capable of maintaining a sufficient pot life and, on the other hand, undergoing quick curing under mild conditions after the start of curing reaction, and by forming or processing the resin composition into a desired sheet shape, an acoustic matching layer having a desired density and high mechanical strength can be formed.

Another object of the present invention is to provide an acoustic matching sheet having a sufficient density and high mechanical strength and a cured product used therefor.

Still another object of the present invention is to provide an acoustic probe including the above acoustic matching sheet as an acoustic matching layer and an acoustic measuring apparatus including the acoustic probe.

Yet still another object of the present invention is to provide a method for producing an acoustic probe including the above acoustic matching sheet as an acoustic matching layer.

To achieve the above objects, the present inventors conducted intensive studies and found that a composition for forming an acoustic matching layer, the composition including metal particles, a specific epoxy resin, a specific polythiol compound serving as a curing agent for the epoxy resin, and a cure-accelerating compound, is capable of maintaining a sufficient pot life and undergoing rapid curing under mild conditions after the start of curing reaction and that a sheet formed by using the composition can be adjusted to have a desired density and also has high mechanical strength. The present invention has been completed by further conducting studies based on this finding.

Thus, the above objects of the present invention have been achieved by the following means.

<1> A resin composition for an acoustic matching layer includes metal particles (A), an epoxy resin (B), a polythiol compound (C), and a cure-accelerating compound (D).

The epoxy resin (B) includes at least one epoxy resin selected from the group consisting of bisphenol A epoxy resins, bisphenol F epoxy resins, and phenol novolac epoxy resins.

The polythiol compound (C) includes a compound having at least two partial structures represented by general formula (1) below or at least two partial structures represented by general formula (2) below.

General formula (1)

General formula (2)

In general formula (1), one of $R^1$ to $R^5$ represents a sulfanyl group, the other four each independently represent a hydrogen atom, an alkyl group having 1 to 10 carbon atoms, or an aryl group having 6 to 14 carbon atoms, and m represents an integer of 0 to 2. When m is 2, two $R^1$ may be the same or different and two $R^5$ may be the same or different. * represents a linking site in the polythiol compound (C).

In general formula (2), one of $R^6$ to $R^{10}$ represents a sulfanyl group, the other four each independently represent a hydrogen atom, an alkyl group having 1 to 10 carbon atoms, or an aryl group having 6 to 14 carbon atoms, and n represents an integer of 0 to 2. When n is 2, two $R^6$ may be the same or different and two $R^{10}$ may be the same or different. * represents a linking site in the polythiol compound (C).

<2> In the resin composition for an acoustic matching layer according to <1>, the polythiol compound (C) is a polythiol compound having at least two partial structures represented by general formula (3) below.

General formula (3)

In general formula (3), $R^{11}$ and $R^{12}$ each independently represent a hydrogen atom or an alkyl group having 1 to 10 carbon atoms, and s represents an integer of 0 to 2. * represents a linking site in the polythiol compound (C).

<3> In the resin composition for an acoustic matching layer according to <2>, in general formula (3), at least one of $R^{11}$ or $R^{12}$ ($R^{11}$ and/or $R^{12}$) represents an alkyl group having 1 to 10 carbon atoms.

<4> In the resin composition for an acoustic matching layer according to <1> or <2>, the polythiol compound (C) is at least one of 1,4-bis(3-mercaptobutyryloxy)butane, pentaerythritol tetrakis(3-mercaptobutyrate), 1,3,5-tris(3-mercaptobutyryloxyethyl)-1,3,5-triazine-2,4,6(1H,3H,5H)-trione, trimethylolpropane tris(3-mercaptobutyrate), ethylene glycol bis(3-mercaptopropionate), tetraethylene glycol bis(3-mercaptopropionate), trimethylolpropane tris(3-mercaptopropionate), pentaerythritol tetrakis(3-mercaptopropionate), dipentaerythritol hexakis(3-mercaptopropionate), or tris[(3-mercaptopropionyloxy)ethyl]isocyanurate.

<5> In the resin composition for an acoustic matching layer according to any one of <1> to <4>, the polythiol compound (C) is at least one of 1,4-bis(3-mercaptobutyryloxy)butane, pentaerythritol tetrakis(3-mercaptobutyrate), 1,3,5-tris(3-mercaptobutyryloxyethyl)-1,3,5-triazine-2,4,6(1H,3H,5H)-trione, or trimethylolpropane tris(3-mercaptobutyrate).

<6> In the resin composition for an acoustic matching layer according to any one of <1> to <5>, the metal particles (A) include a transition metal in groups 4 to 12 of the periodic table.

<7> In the resin composition for an acoustic matching layer according to <6>, the metal particles (A) include a transition metal in period 4 of the periodic table.

<8> In the resin composition for an acoustic matching layer according to any one of <1> to <7>, relative to 100 parts by mass of the content of the metal particles (A), the content of the epoxy resin (B) is 5 to 80 parts by mass, the content of the polythiol compound (C) is 3 to 50 parts by mass, and the content of the cure-accelerating compound (D) is 0.05 to 5 parts by mass.

<9> A cured product is formed by curing the resin composition for an acoustic matching layer according to any one of <1> to <8>.

<10> An acoustic matching sheet includes the cured product according to <9>.

<11> An acoustic probe includes the acoustic matching sheet according to <10> as an acoustic matching layer.

<12> An acoustic measuring apparatus includes the acoustic probe according to <11>.

<13> In the acoustic measuring apparatus according to <12>, the acoustic measuring apparatus is an ultrasound diagnostic apparatus.

<14> A method for producing an acoustic probe includes forming an acoustic matching layer by using the resin composition for an acoustic matching layer according to any one of <1> to <8>.

<15> An acoustic matching layer material set includes a base resin made of a resin composition including metal particles (A) and an epoxy resin (B), and a curing agent including a polythiol compound (C) and a cure-accelerating compound (D).

In the description of the present invention, the expression "to" is meant to include the numerical values before and after "to" as the lower and upper limits.

In the description of the present invention, when the number of carbon atoms of a group is specified, the number of carbon atoms means the number of carbon atoms of the whole group. That is, when the group further has a substituent, the number of carbon atoms means the number of carbon atoms of the whole including the substituent.

In the description of the present invention, when there are a plurality of substituents, a plurality of linking groups, or the like represented by a particular symbol (hereinafter referred to as "substituents or the like") or when a plurality of substituents or the like are simultaneously or alternatively specified, the substituents or the like may be the same or different. Furthermore, even if not specifically stated, when a plurality of substituents or the like are adjacent to each other, they may be linked or fused to each other to form a ring.

The resin composition for an acoustic matching layer and the acoustic matching layer material set according to the present invention are capable of maintaining a sufficient pot life and then undergoing rapid curing under mild conditions. By forming or processing the resin composition or the material set into a desired sheet shape, an acoustic matching sheet having a desired density and high mechanical strength can be obtained.

The acoustic matching sheet according to the present invention has a desired density and high mechanical strength. The cured product according to the present invention is suitable as a constituent material of the acoustic matching layer according to the present invention.

The acoustic probe according to the present invention and the acoustic measuring apparatus including the acoustic probe each have the above acoustic matching sheet as an acoustic matching layer.

According to the method for producing an acoustic probe according to the present invention, the above acoustic probe can be obtained.

DESCRIPTION OF THE PREFERRED EMBODIMENTS

Resin Composition for Acoustic Matching Layer

A resin composition for an acoustic matching layer according to the present invention (hereinafter also referred to simply as "a composition according to the present invention") includes metal particles (A), an epoxy resin (B), a polythiol compound (C), and a cure-accelerating compound (D). The epoxy resin (B), the polythiol compound (C), and the cure-accelerating compound (D) included in the composition according to the present invention fill gaps between the metal particles (A) and function as dispersion media for the metal particles (A). The polythiol compound (C) and the cure-accelerating compound (D) are each a curing component (a component that acts on the epoxy resin (B) to cure it or a component that accelerates the curing).

Due to the above configuration, the composition according to the present invention has a moderately long pot life and, on the other hand, has the property of rapidly curing at low temperature after application. Furthermore, an acoustic matching sheet formed from the composition has high mechanical strength. Although not clear, the reasons for this are presumably as follows.

Probably, the combined use of the polythiol compound (C) and the cure-accelerating compound (D) as curing components makes the initiation reaction of curing mild and ensures the pot life of the composition according to the present invention. Probably, the catalytic action of the cure-accelerating compound (D) to increase the growth reaction rate of curing contributes to the rapid curing of the composition according to the present invention at low temperature. The presence of the metal particles (A) in the composition according to the present invention enables the acoustic matching sheet to be adjusted to have a desired density. In addition, probably, high affinity between the metal particles (A) and the polythiol compound (C) improves the mechanical strength of the sheet.

Metal Particles (A)

The composition according to the present invention contains the metal particles (A). By adjusting the content of the metal particles (A), the density of the composition can be adjusted, and the acoustic impedance of an acoustic matching layer to be obtained can be adjusted to a desired level. The metal particles (A) may be surface treated.

The surface treatment of the metal particles may be performed by any method, and commonly used surface treatment techniques may be used. Examples of treatment methods include oil treatments with hydrocarbon oil, ester oil, lanolin, and the like, silicone treatments with dimethylpolysiloxane, methylhydrogenpolysiloxane, methylphenylpolysiloxane, and the like, fluorine compound treatments with perfluoroalkyl group-containing esters, perfluoroalkylsilanes, perfluoropolyethers, perfluoroalkyl group-containing polymers, and the like, silane coupling agent treatments with 3-methacryloxypropyltrimethoxysilane, 3-glycidoxypropyltrimethoxysilane, and the like, titanate coupling agent treatments with isopropyltriisostearoyl titanate, isopropyltris (dioctylpyrophosphate) titanate, and the like, metallic soap treatments, amino acid treatments with acylglutamic acid and the like, lecithin treatments with hydrogenated egg yolk lecithin and the like, collagen treatments, polyethylene treatments, moisturizing treatments, inorganic compound treatments, and mechanochemical treatments.

There is no particular limitation on a metal constituting the metal particles (A). The metal may be a metal atom alone, a metal carbide, a metal nitride, a metal oxide, a metal boride, or an alloy. Examples of alloys include high-tensile steel (Fe—C), chromium molybdenum steel (Fe—Cr—Mo), manganese molybdenum steel (Fe—Mn—Mo), stainless steel (Fe—Ni—Cr), 42 alloys, Invar (Fe—Ni), permendur (Fe—Co), silicon steel (Fe—Si), red brass, tombac (Cu—Zn), German silver (Cu—Zn—Ni), bronze (Cu—Sn), cupronickel (Cu—Ni), shakudo (Cu—Au), constantan (Cu—Ni), duralumin (Al—Cu), Hastelloy (Ni—Mo—Cr—Fe), Monel (Ni—Cu), Inconel (Ni—Cr—Fe), nichrome (Ni—Cr), ferromanganese (Mn—Fe), and cemented carbide (WC/Co).

From the viewpoint of the affinity for the epoxy resin (B) and the polythiol compound (C), the metal atom constituting the metal particles (A) preferably includes at least one metal atom in groups 4 to 12 of the periodic table.

The metal atom in groups 4 to 12 of the periodic table is preferably a metal atom in period 4 of the periodic table. The use of a metal in period 4 of the periodic table increases the affinity between the metal particles (A) and the epoxy resin (B) that has been cured and effectively contributes to improving the mechanical strength of a sheet to be obtained.

From the viewpoint of breaking energy and sound attenuation, the particle size of the metal particles (A) used in the present invention is preferably 0.01 to 100 μm, more preferably 1 to 10 μm. As used herein, the "particle size" of the metal particles (A) means an average primary particle size.

As used herein, the average primary particle size means a volume average particle size. The volume average particle size is determined as described below.

The metal particles (A) are added to methanol at a concentration of 0.5 mass %, and the mixture is sonicated for 10 minutes to disperse the metal particles (A). The particle size distribution of the metal particles (A) thus treated is measured using a laser diffraction/scattering particle size distribution analyzer (manufactured by Horiba, Ltd., trade name: LA950V2), and the measured volumetric median diameter is used as the volume average particle size. The median diameter corresponds to a particle size at 50% in the particle size distribution represented in cumulative form.

In the composition according to the present invention, the contents of the metal particles (A), the epoxy resin (B), the polythiol compound (C), and the cure-accelerating compound (D) are each appropriately adjusted depending on, for example, the desired acoustic impedance. For example, when the acoustic matching layer is formed of multiple layers, the content of the metal particles (A) in the composition used for the acoustic matching layer on the piezoelectric element side can be relatively high, and the content of the metal particles (A) in the composition used for the acoustic matching layer on the acoustic lens side can be relatively low. This can provide a gradient in acoustic impedance from the piezoelectric element side toward the acoustic lens side, thus further increasing the efficiency of propagation of acoustic waves.

The contents of the epoxy resin (B), the polythiol compound (C), the cure-accelerating compound (D), and the metal particles (A) in the composition according to the present invention may be, for example, as follows: the epoxy resin (B), 5 to 80 parts by mass (preferably 10 to 40 parts by mass, more preferably 15 to 30 parts by mass, still more preferably 15 to 25 parts by mass); the polythiol compound (C), 3 to 50 parts by mass (preferably 5 to 30 parts by mass, more preferably 10 to 20 parts by mass); the cure-accelerating compound (D), 0.05 to 5 parts by mass (preferably 0.15 to 1 part by mass, more preferably 0.2 to 0.6 parts by mass, still more preferably 0.2 to 0.5 parts by mass), relative to 100 parts by mass of the metal particles (A).

Epoxy Resin (B)

The epoxy resin (B) used in the present invention includes at least one epoxy resin selected from the group consisting of bisphenol A epoxy resins, bisphenol F epoxy resins, and phenol novolac epoxy resins.

The bisphenol A epoxy resin used in the present invention is not particularly limited and may be any bisphenol A epoxy resin commonly used as a base resin of an epoxy adhesive. Specific examples of preferred bisphenol A epoxy resins include bisphenol A diglycidyl ethers (jER825, jER828, and jER834 (trade names), manufactured by Mitsubishi Chemical Corporation) and bisphenol A propoxylate diglycidyl ethers (manufactured by Sigma-Aldrich).

The bisphenol F epoxy resin used in the present invention is not particularly limited and may be any bisphenol F epoxy resin commonly used as a base resin of an epoxy adhesive. Specific examples of preferred bisphenol F epoxy resins include bisphenol F diglycidyl ethers (trade name: EPICLON830, manufactured by DIC Corporation) and 4,4'-methylenebis(N,N-diglycidylaniline).

The phenol novolac epoxy resin used in the present invention is not particularly limited and may be any phenol novolac epoxy resin commonly used as a base resin of an epoxy adhesive. Such a phenol novolac epoxy resin is marketed, for example, by Sigma-Aldrich under the product number 406775.

The epoxy resin (B) may be composed of at least one of the above epoxy resins or may include, in addition to at least one of the above epoxy resins, another epoxy resin (e.g., an aliphatic epoxy resin) as long as the effects of the present invention are not impaired. The content of the above three types of epoxy resins (the total content of a bisphenol A epoxy resin, a bisphenol F epoxy resin, and a phenol novolac epoxy resin) in the epoxy resin (B) is preferably 80 mass % or more, more preferably 90 mass % or more.

Polythiol Compound (C)

The polythiol compound (C) used in the present invention is a compound having at least two partial structures represented by general formula (1) below or at least two partial structures represented by general formula (2) below. A structure in which the polythiol compound (C) used in the present invention has three to ten (preferably three to six, more preferably four to six) partial structures represented by general formula (1) below or three to ten (preferably three to six, more preferably four to six) partial structures represented by general formula (2) below is preferred because the crosslink density of a cured product is increased to further improve mechanical properties, particularly, breaking energy.

General formula (1)

General formula (2)

In general formula (1), one of $R^1$ to $R^5$ represents a sulfanyl group (thiol group), the other four each independently represent a hydrogen atom, an alkyl group having 1 to 10 carbon atoms, or an aryl group having 6 to 14 carbon atoms, and m represents an integer of 0 to 2. When m is 2, two IV may be the same or different, and two $R^5$ may be the same or different. * represents a linking site in the polythiol compound (C).

In general formula (2), one of $R^6$ to $R^{10}$ represents a sulfanyl group, the other four each independently represent a hydrogen atom, an alkyl group having 1 to 10 carbon atoms, or an aryl group having 6 to 14 carbon atoms, and n represents an integer of 0 to 2. When n is 2, two $R^6$ may be the same or different, and two $R^{10}$ may be the same or different. * represents a linking site in the polythiol compound (C).

The alkyl group having 1 to 10 carbon atoms may be linear or branched, and examples thereof include methyl, ethyl, propyl, i-propyl, butyl, i-butyl, t-butyl, hexyl, and octyl. Of these, methyl or ethyl is preferred.

Specific examples of the aryl group having 6 to 14 carbon atoms include phenyl and naphthyl.

m is preferably 0 or 1.

n is preferably 0 or 1.

The partial structure represented by general formula (1) above is preferably a partial structure represented by general formula (3) below.

General formula (3)

In general formula (3), $R^{11}$ and $R^{12}$ each independently represent a hydrogen atom or an alkyl group having 1 to 10 carbon atoms, and s represents an integer of 0 to 2. * represents a linking site in the polythiol compound (C).

At least one of $R^{11}$ or $R^{12}$ preferably represents an alkyl group having 1 to 10 carbon atoms.

The alkyl group having 1 to 10 carbon atoms represented by at least one of $R^{11}$ or $R^{12}$ has the same meanings and the same preferred ranges as the above alkyl group that may be employed as $R^1$ in general formula (1).

s is preferably 0 or 1, more preferably 1.

The polythiol compound (C) is preferably an ester of a compound represented by general formula (4) below and a polyfunctional alcohol.

General formula (4)

In general formula (4), $R^1$ to $R^5$ and m have the same meanings and the same preferred ranges as $R^1$ to $R^5$ and m, respectively, in general formula (1) above.

The compound represented by general formula (4) is preferably a compound represented by general formula (5) below.

General formula (5)

In general formula (5), $R^{11}$, $R^{12}$, and s have the same meanings and the same preferred ranges as $R^{11}$, $R^{12}$, and s, respectively, in general formula (3) above.

Specific examples of the compound represented by general formula (4) above include 2-mercaptopropionic acid, 3-mercaptopropionic acid, 3-mercaptobutanoic acid, 2-mercaptoisobutanoic acid, 3-mercapto-3-phenylpropionic acid, 3-mercaptoisobutyric acid, 2-mercapto-3-methylbutyric acid, 3-mercapto-3-methylbutyric acid, 3-mercaptovaleric acid, and 3-mercapto-4-methylvaleric acid.

The polyfunctional alcohol is preferably a bifunctional to decafunctional alcohol (a polyol having 2 to 10 hydroxy groups), more preferably a bifunctional to octafunctional alcohol, particularly preferably a bifunctional to hexafunctional alcohol.

Specific examples of polyfunctional alcohols include alkylene glycols (the number of carbon atoms of an alkylene group is preferably 2 to 10, the alkylene groups may be linear or branched), diethylene glycol, glycerol, dipropylene glycol, trimethylolpropane, pentaerythritol, and dipentaerythritol.

Examples of alkylene glycols include ethylene glycol, trimethylene glycol, 1,2-propane glycol, 1,2-butanediol, 1,3-butanediol, 2,3-butanediol, and tetramethylene glycol.

Preferred polyfunctional alcohols are alkylene glycols whose alkylene main chain has two carbon atoms, such as ethylene glycol, 1,2-propane glycol, and 1,2-butanediol, trimethylolpropane, and pentaerythritol.

Specific examples of the polythiol compound (C) include, but are not limited to, the following.

Specific examples include bis(1-mercaptoethyl) phthalate, bis(2-mercaptopropyl) phthalate, bis(3-mercaptobutyl) phthalate, bis(3-mercaptoisobutyl) phthalate, ethylene glycol bis(3-mercaptopropionate), ethylene glycol bis(3-mercaptobutyrate), propylene glycol bis(3-mercaptobutyrate), diethylene glycol bis(3-mercaptobutyrate), tetraethylene glycol bis(3-mercaptopropionate), butanediol bis(3-mercaptobutyrate), octanediol bis(3-mercaptobutyrate), trimethylolpropane tris(3-mercaptobutyrate), trimethylolpropane tris(3-mercaptopropionate), dipentaerythritol hexakis(3-mercaptopropionate), pentaerythritol tetrakis(3-mercaptopropionate), pentaerythritol tetrakis(3-mercaptobutyrate), dipentaerythritol hexakis(3-mercaptobutyrate), ethylene glycol bis(2-mercaptopropionate), propylene glycol bis(2-mercaptopropionate), diethylene glycol bis(2-mercaptopropionate), butanediol bis(2-mercaptopropionate), octanediol bis(2-mercaptopropionate), trimethylolpropane tris(2-mercaptopropionate), pentaerythritol tetrakis(2-mercaptopropionate), dipentaerythritol hexakis(2-mercaptopropionate), ethylene glycol bis(3-mercaptoisobutyrate), propylene glycol bis(3-mercaptoisobutyrate), diethylene glycol bis(3-mercaptoisobutyrate), butanediol bis(3-mercaptoisobutyrate), octanediol bis(3-mercaptoisobutyrate), trimethylolpropane tris(3-mercaptoisobutyrate), pentaerythritol tetrakis(3-mercaptoisobutyrate), dipentaerythritol hexakis(3-mercaptoisobutyrate), ethylene glycol bis(2-mercaptoisobutyrate), propylene glycol bis(2-mercaptoisobutyrate), diethylene glycol bis(2-mercaptoisobutyrate), butanediol bis(2-mercaptoisobutyrate), octanediol bis(2-mercaptoisobutyrate), trimethylolpropane tris(2-mercaptoisobutyrate), pentaerythritol tetrakis(2-mercaptoisobutyrate), dipentaerythritol hexakis(2- mercaptoisobutyrate), ethylene glycol bis(4-mercaptovalerate), propylene glycol bis(4-mercaptoisovalerate), diethylene glycol bis(4-mercaptovalerate), butanediol bis(4-mercaptovalerate), octanediol bis(4-mercaptovalerate), trimethylolpropane tris (4-mercaptovalerate), pentaerythritol tetrakis(4-mercaptovalerate), dipentaerythritol hexakis(4-mercaptovalerate), ethylene glycol bis(3-mercaptovalerate), propylene glycol bis(3-mercaptovalerate), diethylene glycol bis(3-mercaptovalerate), butanediol bis(3-mercaptovalerate), octanediol bis(3-mercaptovalerate), trimethylolpropane tris(3-mercaptovalerate), pentaerythritol tetrakis(3-mercaptovalerate), dipentaerythritol hexakis(3-mercaptovalerate), 1,4-bis(3-mercaptobutyryloxy)butane, 1,3,5-tris(3-mercaptobutyryloxyethyl)-1,3,5-triazine-2,4,6(1H,3H,5H)-trione, and tris [(3-mercaptopropionyloxy)ethyl] isocyanurate.

The polythiol compound (C) is preferably at least one of 1,4-bis(3-mercaptobutyryloxy)butane, pentaerythritol tetrakis(3-mercaptobutyrate), 1,3,5-tris(3-mercaptobutyryloxyethyl)-1,3,5-triazine-2,4,6(1H,3H,5H)-trione, trimethylolpropane tris(3-mercaptobutyrate), ethylene glycol bis(3-mercaptopropionate), tetraethylene glycol bis(3-mercaptopropionate), trimethylolpropane tris(3-mercaptopropionate), pentaerythritol tetrakis(3-mercaptopropionate), dipentaerythritol hexakis(3-mercaptopropionate), or tris[(3-mercaptopropionyloxy) ethyl] isocyanurate, preferably at least one of 1,4-bis(3-mercaptobutyryloxy)butane, pentaerythritol tetrakis(3-mercaptobutyrate), 1,3,5-tris(3-mercaptobutyryloxyethyl)-1,3,5-triazine-2,4,6(1H,3H,5H)-trione, or trimethylolpropane tris(3-mercaptobutyrate), because these compounds have little odor and a desired degree of viscosity and mix well with the epoxy resin (B) and because a mixture obtained by mixing the metal particles (A), the epoxy resin (B), and curing components is easy to handle.

The molecular weight of the polythiol compound (C) is not particularly limited but preferably 200 to 1,000, more preferably 300 to 800, because a polythiol compound (C) having such a molecular weight is easily mixed with and less easily separated from the epoxy resin (B) of an adhesive of the present invention and because a mixture obtained by mixing a base resin and a curing agent is easy to handle, for example, less likely to drip or become uneven.

In the present invention, the polythiol compound (C) may be a commercially available product, specific examples of which include 1,4-bis(3-mercaptobutyryloxy)butane (trade name: Karenz MT BD1, manufactured by Showa Denko K.K.), pentaerythritol tetrakis(3-mercaptobutyrate) (trade name: Karenz MT PE1, manufactured by Showa Denko K. K.), 1,3,5-tris(3-mercaptobutyryloxyethyl)-1,3,5-triazine-2, 4,6(1H,3H,5H)-trione (trade name: Karenz MT NR1, manufactured by Showa Denko K.K.), and trimethylolpropane tris(3-mercaptobutyrate) (trade name TPMB, manufactured by Showa Denko K.K.).

In the present invention, the polythiol compound (C) may be composed of a single compound or a combination of two or more compounds.

The polythiol compound (C) may be composed of at least one of the above polythiol compounds or may include, in addition to at least one of the above polythiol compounds, another polythiol compound as long as the effects of the present invention are not impaired. The content of the above polythiol compounds (the total content of the compound having at least two partial structures represented by general formula (1) and the compound having at least two partial structures represented by general formula (2)) in the polythiol compound (C) is preferably 80 mass % or more, more preferably 90 mass % or more.

Cure-Accelerating Compound (D)

The cure-accelerating compound (D) used in the present invention has a reaction activity starting temperature of as low as −20° C. to 23° C. and accelerates curing of the epoxy resin (B).

Examples of the cure-accelerating compound (D) used in the present invention include, but are not limited to, amine compounds, guanidine compounds, imidazol compounds, and phosphonium compounds. Amine compounds and imidazol compounds are preferred because the rate of cure increases to increase the degree of cure.

Examples of amine compounds include, but are not limited to, trialkylamines such as triethylamine and tributylamine and amine compounds such as 4-dimethylaminopyridine, benzyldimethylamine, 2,4,6,-tris (dimethylaminomethyl) phenol, 1,8-diazabicyclo[5.4.0]-7-undecene (DBU), and 1,5-diazabicyclo[4.3.0]-nonene (DBN).

Examples of guanidine compounds include, but are not limited to, dicyandiamide, 1-methylguanidine, 1-ethylguanidine, 1-cyclohexylguanidine, 1-phenylguanidine, 1-(o-tolyl)guanidine, 1,1-dimethylguanidine, 1,3-diphenylguanidine, 1,2,3-trimethylguanidine, 1,1,3,3-tetramethylguanidine, 1,1,2,3,3-pentamethylguanidine, 1,5,7-triazabicyclo[4.4.0]dec-5-ene, 7-methyl-1,5,7-triazabicyclo[4.4.0]dec-5-ene, 1-methylbiguanide, 1-ethylbiguanide, 1-n-butylbiguanide, 1-n-octadecylbiguanide, 1,1-dimethylbiguanide, 1,1-diethylbiguanide, 1-cyclohexylbiguanide, 1-allylbiguanide, 1-phenylbiguanide, and 1-(o-tolyl)biguanide.

Examples of imidazol compounds include, but are not limited to, imidazol compounds such as 2-methylimidazole, 2-undecylimidazole, 2-heptadecylimidazole, 1,2-dimethylimidazole, 2-ethyl-4-methylimidazole, 2-phenylimidazole, 4-methyl-2-phenylimidazole, 1-benzyl-2-methylimidazole, 1-benzyl-2-phenylimidazole, 1-(2-cyanoethyl)-2-methylimidazole, 1-(2-cyanoethyl)-2-undecylimidazole, 1-(2-cyanoethyl)-2-ethyl-4-methylimidazole, 1-(2-cyanoethyl)-2-phenylimidazole, 1-(2-cyanoethyl)-2-undecylimidazolium trimellitate, 1-(2-cyanoethyl)-2-phenylimidazolium trimellitate, 2,4-diamino-6-[2-(2'-methyl-1'-imidazolyl)ethyl]-s-triazine, 2,4-diamino-6-[2-(2'-undecyl-1'-imidazolyl)ethyl]-s-triazine, 2,4-diamino-6-[2-(2'-ethyl-4'-methyl-1'-imidazolyl)ethyl]-s-triazine, 2,4-diamino-6-[2-(2'-methyl-1'-imidazolyl)ethyl]-s-triazine isocyanuric acid adducts, 2-phenylimidazole isocyanuric acid adducts, 4,5-bis(hydroxymethyl)-2-phenylimidazole, 5-hydroxymethyl-4-methyl-2-phenylimidazole, 2,3-dihydro-1H-pyrrolo[1,2-a] benzimidazole, 1-dodecyl-2-methyl-3-benzylimidazolium chloride, 2-methylimidazoline, 2-phenylimidazoline, and 1-(2-hydroxy-3-phenoxy)propyl-2-methylimidazole; and adducts of imidazol compounds and epoxy resins.

Examples of phosphonium compounds include, but are not limited to, tetraphenylphosphonium bromide, tetrabutylphosphonium bromide, butyltriphenylphosphonium bromide, tetraphenylphosphonium iodide, tetrabutylphosphonium iodide, butyltriphenylphosphonium iodide, tetraphenylphosphonium tetraphenylborate, tetrabutylphosphonium tetraphenylborate, butyltriphenylphosphonium tetraphenylborate, tetraphenylphosphonium tetrabutylborate, tetrabutylphosphonium tetrabutylborate, butyltriphenylphosphonium tetrabutylborate, tetraphenylphosphonium acetate, tetrabutylphosphonium acetate, butyltriphenylphosphonium acetate, tetrabutylphosphonium tetrafluoroborate, tetrabutylphosphonium hexafluorophosphate, methyltributylphosphonium dimethylphosphate, tetrabutylphosphonium acetate, tetrabutylphosphonium hydroxide, tetrabutylphosphonium chloride, and tetraphenylphosphonium chloride. Of these, from the viewpoint of reactivity and transparency, tetrabutylphosphonium bromide, methyltributylphosphonium dimethylphosphate, tetrabutylphosphonium chloride, tetrabutylphosphonium iodide, tetrabutylphosphonium tetraphenylborate, tetraphenylphosphonium bromide, tetraphenylphosphonium chloride, tetraphenylphosphonium iodide, and tetraphenylphosphonium tetraphenylborate are preferred, and methyltributylphosphonium dimethylphosphate and tetrabutylphosphonium bromide are more preferred.

In the present invention, the cure-accelerating compound (D) may be composed of a single compound or a combination of two or more compounds.

In the composition according to the present invention, curing reaction of the epoxy resin (B) may proceed over time. Accordingly, the properties of the composition may change over time, thus being unstable. However, for example, if the composition is preserved at a temperature of −10° C. or lower, the composition can be brought into a state in which each component is stably maintained with no curing reaction occurring or with curing reaction sufficiently inhibited.

It is also preferred that a resin composition including the epoxy resin (B) and the metal particles (A) be used as a base resin and that the base resin and a curing agent including the curing components (the polythiol compound (C) and the cure-accelerating compound (D)) be used in the form of an acoustic matching layer material set in which the base resin and the curing agent are separate from each other. In forming an acoustic matching layer, the base resin and the curing agent are mixed together to prepare the composition according to the present invention, and a layer is formed using the composition, whereby the acoustic matching layer can be formed.

In the composition according to the present invention, the mass ratio of the epoxy resin (B) to the curing components may be, for example, 99/1 to 20/80, and is preferably 90/10 to 40/60. The mass ratio of the epoxy resin (B) to the curing components may be 80/20 to 40/60 or 70/30 to 40/60. The mass ratio of the polythiol compound (C) to the cure-accelerating compound (D) is preferably 99.9/0.1 to 90/10. The mass ratio of the polythiol compound (C) to the cure-accelerating compound (D) may be 99.9/0.1 to 94/6.

When the composition according to the present invention is prepared by using the above acoustic matching layer material set and mixing the base resin and the curing agent together in forming a layer, the base resin and the curing agent are preferably mixed together such that the mass ratio of the epoxy resin (B) to the curing components is 99/1 to 20/80, more preferably 90/10 to 40/60. The base resin and the curing agent may be mixed together such that the mass ratio of the epoxy resin (B) to the curing components is 80/20 to 40/60 or 70/30 to 40/60. The base resin and the curing agent are preferably mixed together such that the mass ratio of the polythiol compound (C) to the cure-accelerating compound (D) is 99.9/0.1 to 90/10. The base resin and the curing agent may be mixed together such that the mass ratio of the polythiol compound (C) to the cure-accelerating compound (D) is 99.9/0.1 to 94/6.

The composition according to the present invention may be composed of the epoxy resin (B), the curing components, and the metal particles (A). The composition may also contain other component as long as the effects of the present invention are not impaired. As the component other than the epoxy resin (B) and the curing components and other than the metal particles (A), for example, a curing retarder, a solvent, a dispersant, a pigment, a dye, an antistatic agent, an antioxidant, a flame retardant, or a thermal conductivity improver can be appropriately added.

In the composition according to the present invention, the sum of the contents of the epoxy resin (B), the curing components, and the metal particles (A) is preferably 80 mass % or more, more preferably 90 mass % or more.

Preparation of Resin Composition for Acoustic Matching Layer

The resin composition for an acoustic matching layer according to the present invention can be obtained, for example, by kneading the components of the resin composition for an acoustic matching layer with a kneader, a pressure kneader, a Banbury mixer (continuous kneader), a two-roll kneading apparatus, or the like. This can provide a resin composition for an acoustic matching layer, the resin composition including an epoxy resin (B), curing components, and metal particles (A) dispersed therein.

When an acoustic matching layer material set that includes a base resin made of a resin composition including an epoxy resin (B) and metal particles (A) and includes a curing agent including curing components is provided, the base resin can be obtained by kneading the epoxy resin (B) and the metal particles (A). When an acoustic matching layer is produced, the base resin and the curing agent are mixed together to obtain the composition according to the present invention. The composition is cured while being shaped, whereby the acoustic matching layer or a precursor sheet thereof can be formed.

Acoustic Matching Sheet (Acoustic Matching Layer)

By forming the composition according to the present invention into a sheet shape and optionally, for example, cutting or dicing the sheet to a desired thickness or shape, an acoustic matching sheet can be obtained. The acoustic matching sheet is used as an acoustic matching layer of an acoustic probe. The configuration of an acoustic probe including an acoustic matching layer will be described later.

In producing the sheet, the composition is formed into a desired sheet shape at a low temperature at which no curing reaction occurs or curing proceeds slowly, and then the shaped product is cured, for example, by heating if necessary, to provide an acoustic matching sheet or a precursor sheet thereof. That is, the acoustic matching sheet according to the present invention is a cured product having a three-dimensional network structure formed by curing the composition according to the present invention.

Acoustic Probe

An acoustic probe according to the present invention has, as an acoustic matching layer, an acoustic matching sheet formed by using the composition according to the present invention.

Figure 1:
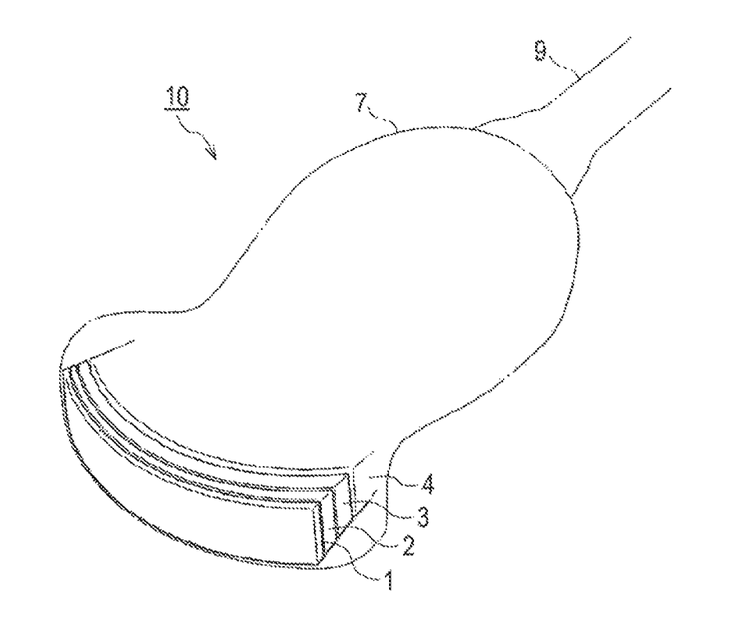
FIG. 1 is a perspective view of an example of a convex ultrasound probe, which is one aspect of an acoustic probe.

An exemplary configuration of the acoustic probe according to the present invention is shown in FIG. 1. The acoustic probe shown in FIG. 1 is an ultrasound probe of an ultrasound diagnostic apparatus. An ultrasound probe uses, particularly, ultrasonic waves as acoustic waves for an acoustic probe. Thus, the basic structure of an ultrasound probe can be applied to an acoustic probe without any change.

Ultrasound Probe

An ultrasound probe 10, which is a main component part of an ultrasound diagnostic apparatus, has a function to generate ultrasonic waves as well as to transmit and receive ultrasonic beams. The ultrasound probe 10 has a configuration in which an acoustic lens 1, an acoustic matching layer 2, a piezoelectric element layer 3, and a backing member 4 are disposed in this order from a distal end (a surface to be in contact with a living body, or a subject) portion, as shown in FIG. 1. In recent years, ultrasound probes have also been proposed in which, for the purpose of receiving a high-order harmonic, a transmitting ultrasonic transducer (piezoelectric element) and a receiving ultrasonic transducer (piezoelectric element) are made of different materials to form a multilayer structure. Piezoelectric element layer The piezoelectric element layer 3 is a portion that generates ultrasonic waves, and electrodes are affixed to opposite sides of a piezoelectric element. When a voltage is applied, the piezoelectric element oscillates by repeating expansion and contraction to thereby generate ultrasonic waves.

As materials constituting piezoelectric elements, what is called ceramic inorganic piezoelectric bodies, which are obtained by polarizing single crystals of quartz, $LiNbO_3$, $LiTaO_3$, $KNbO_3$, and the like, thin films of ZnO, AlN, and the like, and $PbO_3$ ($ZrO_3$, $TiO_3$) sintered bodies, are widely used. In general, piezoelectric ceramics with high conversion efficiency, such as lead zirconate titanate (PZT), are used.

A piezoelectric element for detecting received waves on the high-frequency side is required to have sensitivity over a wider bandwidth. Thus, as a piezoelectric element suitable for a high frequency and a wide band, an organic piezoelectric body obtained using an organic macromolecular substance such as polyvinylidene fluoride (PVDF) is used.

Furthermore, for example, JP2011-071842A discloses a capacitive micromachined ultrasonic transducer (cMUT) that exhibits excellent short-pulse characteristics and wideband characteristics, is suitable for mass production, provides an array structure with little variation in characteristics, and is obtained by using micro electro mechanical systems (MEMS).

In the present invention, any of the piezoelectric element materials can be preferably used.
Backing Member The backing member 4, which is disposed in the back of the piezoelectric element layer 3, suppresses an excessive oscillation to shorten the pulse width of ultrasonic waves, thus contributing to improving the axial resolution in an ultrasound diagnostic image.
Acoustic Matching Layer The acoustic matching layer 2 is disposed in order to achieve efficient transmission and reception of ultrasonic waves by reducing the difference in acoustic impedance between the piezoelectric element layer 3 and a subject.
Acoustic Lens The acoustic lens 1 is disposed in order to converge ultrasonic waves in a slice direction by utilizing refraction to improve resolving power. The acoustic lens 1 comes into close contact with a living body, or a subject, and is required to match ultrasonic waves to the acoustic impedance of the living body (in the case of a human body, 1.4 to $1.7 \times 10^6$ $kg/m^2/sec$), and the amount of ultrasonic wave attenuation in the acoustic lens 1 itself is required to be small.

That is, by using, as a material for the acoustic lens 1, such a material that the sound velocity in the material is sufficiently lower than the sound velocity in a human body and that causes less ultrasonic wave attenuation and has an acoustic impedance value close to that of human body skin, the sensitivity to transmit and receive ultrasonic waves are increased.

The operation of the ultrasound probe 10 having such a configuration will be described. A voltage is applied to the electrodes disposed on the opposite sides of the piezoelectric element to resonate the piezoelectric element layer 3, thus transmitting an ultrasonic signal from the acoustic lens to a subject. At the time of reception, the piezoelectric element layer 3 is oscillated by a reflected signal (echo signal) from the subject, and the oscillation is electrically converted into a signal to obtain an image.
Method for Producing Acoustic Probe The acoustic probe according to the present invention can be produced by a usual method provided that the resin composition for an acoustic matching layer according to the present invention is used. That is, a method for producing an acoustic probe according to the present invention includes forming an acoustic matching layer on a piezoelectric element by using the resin composition for an acoustic matching layer according to the present invention. The piezoelectric element can be provided on a backing member by a usual method.

Furthermore, an acoustic lens is formed on the acoustic matching layer by a usual method using a material for forming the acoustic lens.
Acoustic Measuring Apparatus An acoustic measuring apparatus according to the present invention has the acoustic probe according to the present invention. The acoustic measuring apparatus has functions, for example, to display the signal strength of a signal received by the acoustic probe and to translate the signal into an image.

The acoustic measuring apparatus according to the present invention may be an ultrasonic measuring apparatus including an ultrasound probe.

EXAMPLES

The present invention will now be described in more detail with reference to examples in which ultrasonic waves are used as acoustic waves. It should be noted that in the present invention, not only ultrasonic waves but also any acoustic waves of audio frequencies may be used as long as appropriate frequencies are selected according to the subject, the measurement conditions, and so on. The term "room temperature" means 25° C. Preparation example of resin composition for acoustic matching layer of Example 1

Metal particles (A-1), an epoxy resin (B-1), a polythiol compound (C-1), and a cure-accelerating compound (D-1) in amounts shown in Table 1 below were mixed together. Specifically, the metal particles (A-1) and the epoxy resin (B-1) were stirred for 4 minutes at 1800 rpm under a reduced pressure of 1.0 Pa at room temperature using a stirrer (trade name: THINKY MIXER ARV-310, manufactured by THINKY CORPORATION) while being defoamed. The polythiol compound (C-1) and the cure-accelerating compound (D-1) were added thereto, and the resulting mixture was again stirred and defoamed under the same conditions. In this manner, a resin composition for an acoustic matching layer of Example 1 was obtained.

Resin compositions for acoustic matching layers of Examples other than Example 1 shown in Table 1 below were prepared in the same manner as the resin composition for an acoustic matching layer of Example 1 except that compositions shown in Table 1 below were used.
Pot Life For the above-prepared resin compositions for acoustic matching layers, the heat generation starting time at 23° C. was determined using a differential scanning calorimeter (DSC). The results are shown in Table 1. In this test, A to C are acceptable.

Evaluation Criteria

A: Heat generation did not start after 30 minutes.

B: Heat generation started after more than 15 minutes and within 30 minutes.

C: Heat generation started after more than 1 minute and within 15 minutes.

D: Curing was already completed during mixing.

Low-Temperature Curing Properties

For the above-prepared resin compositions for acoustic matching layers, the exothermic peak (maximum) at 10° C. was determined with a differential scanning calorimeter (DSC), and the curing properties at low temperature was evaluated according to the following evaluation criteria. The results are shown in Table 1. In this test, A to C are acceptable.

Evaluation Criteria

A: An exothermic peak was observed within 4 hours.

B: An exothermic peak was observed after more than 4 hours and within 8 hours.

C: An exothermic peak was observed after more than 8 hours and within 12 hours.

D: No exothermic peaks were observed within 12 hours.

Density

The above-prepared resin compositions for acoustic matching layers were each cured at 80° C. for 18 hours and then cured at 150° C. for 1 hour with a MINI TEST PRESS (manufactured by Toyo Seiki Seisaku-sho, Ltd.) to obtain acoustic matching sheets 60 mm long×60 mm wide×2 mm thick.

For the sheets obtained, the density at 25° C. was measured in accordance with a density measuring method of the A method (water displacement method) described in JIS K7112 (1999) by using an electronic densimeter (manufactured by Alfa Mirage Co., Ltd., trade name "SD-200L").

Breaking Energy

From the above-prepared resin compositions for acoustic matching layers, acoustic matching sheets 50 mm long×50 mm wide×0.4 mm thick were obtained in the same manner as described above. From each acoustic matching sheet, a strip specimen 40 mm long×5 mm wide×0.4 mm thick was punched out. The specimen was subjected to a tensile test at a tensile speed of 30 mm/min using a tensile tester (Autograph AGS-X/20N, manufactured by Shimadzu Corporation) and evaluated for breaking energy according to the following evaluation criteria. The results are shown in Table 1. In this test, A to C are acceptable.

Evaluation Criteria

A: 50 J or more

B: 40 J or more and less than 50 J

C: 30 J or more and less than 40 J

D: Less than 30 J

The results are shown in Tables below.

TABLE 1

| | | Example 1 | Example 2 | Example 3 | Example 4 | Example 5 | Example 6 | Example 7 | Example 8 | Example 9 | Example 10 | Example 11 | Example 12 |
|---|---|---|---|---|---|---|---|---|---|---|---|---|---|
| Metal particles (A) | Type | (A-1) Fe | (A-2) Zn | (A-3) Ti | (A-4) Cu | (A-5) Ni | (A-6) Zr | (A-7) Mo | (A-8) Ag | (A-9) Pt | (A-10) Au | (A-1) Fe | (A-1) Fe |
| | Content [parts by mass] | 100 | 100 | 100 | 100 | 100 | 100 | 100 | 100 | 100 | 100 | 100 | 100 |
| Epoxy resin (B) | Type | (B-1) | (B-1) | (B-1) | (B-1) | (B-1) | (B-1) | (B-1) | (B-1) | (B-1) | (B-1) | (B-2) | (B-3) |
| | Content [parts by mass] | 20 | 20 | 20 | 20 | 20 | 20 | 20 | 20 | 20 | 20 | 20 | 20 |
| Polythiol compound (C) | Type | (C-1) | (C-1) | (C-1) | (C-1) | (C-1) | (C-1) | (C-1) | (C-1) | (C-1) | (C-1) | (C-1) | (C-1) |
| | Content [parts by mass] | 12 | 12 | 12 | 12 | 12 | 12 | 12 | 12 | 12 | 12 | 12 | 12 |
| Cure-accelerating compound (D) | Type | (D-1) | (D-1) | (D-1) | (D-1) | (D-1) | (D-1) | (D-1) | (D-1) | (D-1) | (D-1) | (D-1) | (D-1) |
| | Content [parts by mass] | 0.3 | 0.3 | 0.3 | 0.3 | 0.3 | 0.3 | 0.3 | 0.3 | 0.3 | 0.3 | 0.3 | 0.3 |
| Pot life | | A | A | A | A | A | A | A | A | A | A | A | A |
| 10° C. curing properties | | A | A | A | A | A | A | A | A | A | A | A | A |
| Density [g/cm$^3$] | | 3.3 | 3.2 | 2.7 | 3.4 | 3.4 | 3.1 | 3.6 | 3.6 | 4.2 | 4.2 | 3.3 | 3.3 |
| Breaking energy | | A | A | A | A | A | B | B | B | B | B | A | A |

TABLE 2

| | | Example 13 | Example 14 | Example 15 | Example 16 | Example 17 | Example 18 | Example 19 | Example 20 | Example 21 | Example 22 | Example 23 | Example 24 |
|---|---|---|---|---|---|---|---|---|---|---|---|---|---|
| Metal particles (A) | Type | (A-1) Fe | (A-1) Fe | (A-1) Fe | (A-1) Fe | (A-1) Fe | (A-1) Fe | (A-1) Fe | (A-1) Fe | (A-1) Fe | (A-1) Fe | (A-1) Fe | (A-1) Fe |
| | Content [parts by mass] | 100 | 100 | 100 | 100 | 100 | 100 | 100 | 100 | 100 | 100 | 100 | 100 |
| Epoxy resin (B) | Type | (B-4) | (B-5) | (B-6) | (B-7) | (B-1) | (B-1) | (B-1) | (B-1) | (B-1) | (B-1) | (B-1) | (B-1) |
| | Content [parts by mass] | 20 | 20 | 20 | 20 | 20 | 20 | 20 | 20 | 20 | 20 | 20 | 20 |

TABLE 2-continued

|  |  | Example 13 | Example 14 | Example 15 | Example 16 | Example 17 | Example 18 | Example 19 | Example 20 | Example 21 | Example 22 | Example 23 | Example 24 |
|---|---|---|---|---|---|---|---|---|---|---|---|---|---|
| Polythiol compound (C) | Type | (C-1) | (C-1) | (C-1) | (C-1) | (C-2) | (C-3) | (C-4) | (C-5) | (C-6) | (C-7) | (C-8) | (C-9) |
|  | Content [parts by mass] | 12 | 12 | 12 | 12 | 12 | 12 | 12 | 12 | 12 | 12 | 12 | 12 |
| Cure-accelerating compound (D) | Type | (D-1) | (D-1) | (D-1) | (D-1) | (D-1) | (D-1) | (D-1) | (D-1) | (D-1) | (D-1) | (D-1) | (D-1) |
|  | Content [parts by mass] | 0.3 | 0.3 | 0.3 | 0.3 | 0.3 | 0.3 | 0.3 | 0.3 | 0.3 | 0.3 | 0.3 | 0.3 |
| Pot life |  | A | A | A | A | A | A | A | C | B | B | B | C |
| 10° C. curing properties |  | A | A | A | A | A | A | A | A | A | A | A | A |
| Density [g/cm³] |  | 3.3 | 3.3 | 3.3 | 3.3 | 3.3 | 3.3 | 3.3 | 3.3 | 3.3 | 3.3 | 3.3 | 3.3 |
| Breaking energy |  | A | A | A | A | C | B | B | C | C | B | A | A |

TABLE 3

|  |  | Example 25 | Example 26 | Example 27 | Example 28 | Example 29 | Example 30 | Example 31 | Example 32 | Example 33 | Example 34 | Comparative Example 1 | Comparative Example 2 | Comparative Example 3 |
|---|---|---|---|---|---|---|---|---|---|---|---|---|---|---|
| Metal particles (A) | Type | (A-1) Fe | (A-1) Fe | (A-1) Fe | (A-1) Fe | (A-1) Fe | (A-1) Fe | (A-1) Fe | (A-1) Fe | (A-1) Fe | (A-1) Fe | (A-1) Fe | (A-1) Fe | (A-1) Fe |
|  | Content [parts by mass] | 100 | 100 | 100 | 100 | 100 | 100 | 100 | 100 | 100 | 100 | 100 | 100 | 100 |
| Epoxy resin (B) | Type | (B-1) | (B-1) | (B-1) | (B-1) | (B-1) | (B-1) | (B-1) | (B-1) | (B-1) | (B-1) | (B-1) | (B-1) | (B-1) |
|  | Content [parts by mass] | 20 | 20 | 20 | 20 | 20 | 20 | 10 | 15 | 30 | 40 | 20 | 20 | 20 |
| Polythiol compound (C) | Type | (C-10) | (C-1) | (C-1) | (C-1) | (C-1) | (C-1) | (C-1) | (C-1) | (C-1) | (C-1) | (C-1) | (E-1) | (E-2) |
|  | Content [parts by mass] | 12 | 12 | 12 | 20 | 8 | 6 | 6 | 9 | 18 | 24 | 12 | 12 | 12 |
| Cure-accelerating compound (D) | Type | (D-1) | (D-2) | (D-3) | (D-1) | (D-1) | (D-1) | (D-1) | (D-1) | (D-1) | (D-1) | — | — | (D-1) |
|  | Content [parts by mass] | 0.3 | 0.3 | 0.3 | 0.6 | 0.3 | 0.15 | 0.15 | 0.23 | 0.45 | 0.6 |  |  | 0.3 |
| Pot life |  | B | A | C | B | A | A | A | A | B | C | A | A | D |
| 10° C. curing properties |  | A | A | B | A | B | C | A | A | A | A | D | D | D |
| Density [g/cm³] |  | 3.3 | 3.3 | 3.3 | 3.0 | 3.5 | 3.6 | 4.4 | 3.7 | 2.7 | 2.4 | 3.3 | 3.3 | 3.3 |
| Breaking energy |  | B | A | B | A | A | B | C | B | A | A | C | A | A |

Details of the components shown in Tables above are as follows.

Metal Particles (A)
(A-1) Fe (average particle size: 4.1 μm)
(A-2) Zn (average particle size: 6.3 μm)
(A-3) Ti (average particle size: 5.1 μm)
(A-4) Cu (average particle size: 3.6 μm)
(A-5) Ni (average particle size: 2.6 μm)
(A-6) Zr (average particle size: 6.1 μm)
(A-7) Mo (average particle size: 4.4 μm)
(A-8) Ag (average particle size: 5.6 μm)
(A-9) Pt (average particle size: 6.8 μm)
(A-10) Au (average particle size: 3.0 μm)

Epoxy Resin (B)
(B-1) Bisphenol A diglycidyl ether ("jER825" (trade name) manufactured by Mitsubishi Chemical Corporation, epoxy equivalent weight: 170)
(B-2) Bisphenol A diglycidyl ether ("jER828" (trade name) manufactured by Mitsubishi Chemical Corporation, epoxy equivalent weight: 190)
(B-3) Bisphenol A diglycidyl ether ("jER834" (trade name) manufactured by Mitsubishi Chemical Corporation, epoxy equivalent weight: 230)
(B-4) Bisphenol F diglycidyl ether ("EPICLON830" (trade name) manufactured by DIC Corporation, epoxy equivalent weight: 170)
(B-5) Epoxy novolac resin (manufactured by Sigma-Aldrich, product number 406775, epoxy equivalent weight: 170)
(B-6) Bisphenol A propoxylate diglycidyl ether (manufactured by Sigma-Aldrich, epoxy equivalent weight: 228)
(B-7) 4,4'-Methylenebis(N,N-diglycidylaniline) (manufactured by Tokyo Chemical Industry Co., Ltd., epoxy equivalent weight: 106)

Polythiol compound (C)

(C-1) Pentaerythritol tetrakis(3-mercaptobutyrate) (manufactured by Showa Denko K.K., trade name "Karenz MT PE1")
(C-2) 1,4-Bis(3-mercaptobutyryloxy)butane (manufactured by Showa Denko K.K., trade name "Karenz MT BD1")
(C-3) 1,3,5-Tris(3-mercaptobutyryloxyethyl)-1,3,5-triazine-2,4,6(1H,3H,5H)-trione (manufactured by Showa Denko K.K., trade name "Karenz MT NR1")
(C-4) Trimethylolpropane tris(3-mercaptobutyrate) (manufactured by Showa Denko K.K., trade name "TPMB")
(C-5) Ethylene glycol bis(3-mercaptopropionate) (reagent manufactured by Wako Pure Chemical Industries, Ltd.)
(C-6) Tetraethylene glycol bis(3-mercaptopropionate) (manufactured by Sakai Chemical Industry Co., Ltd., trade name "EGMP-4")
(C-7) Trimethylolpropane tris(3-mercaptopropionate) (manufactured by Sakai Chemical Industry Co., Ltd., trade name "TMMP")
(C-8) Pentaerythritol tetrakis(3-mercaptopropionate) (manufactured by Sakai Chemical Industry Co., Ltd., trade name "PEMP")
(C-9) Dipentaerythritol hexakis(3-mercaptopropionate) (manufactured by Sakai Chemical Industry Co., Ltd., trade name "DPMP")
(C-10) Tris[(3-mercaptopropionyloxy)ethyl] isocyanurate (manufactured by Sakai Chemical Industry Co., Ltd., trade name "TEMPIC") Cure-accelerating compound (D)
(D-1) 2,4,6-Tris(dimethylaminomethyl) phenol (manufactured by Nacalai Tesque, Inc., trade name "LUVEAK DMP-30")
(D-2) 2-Ethyl-4-methylimidazole (reagent manufactured by Tokyo Chemical Industry Co., Ltd.)
(D-3) Tetraphenylphosphonium bromide (manufactured by Hokko Chemical Industry Co., Ltd., trade name "TPP-PB") Other curing agent (given in line of Polyol compound (C) for comparison)
(E-1) Polyamidoamine (manufactured by DIC Corporation, trade name "LUCKAMIDE EA-330")
(E-2) Triethylenetetramine (reagent manufactured by Tokyo Chemical Industry Co., Ltd.)

As shown in Table 1 above, the resin compositions for acoustic matching not satisfying the requirements of the present invention were poor in at least low-temperature curing properties (Comparative Examples 1 to 3). The resin composition for acoustic matching of Comparative Example 3, including (E-2) triethylenetetramine and (D-1) 2,4,6-tris (dimethylaminomethyl) phenol as curing components, was poor also in pot life. This is probably because the time from when the composition was prepared until curing reaction started was reduced by the action of the cure-accelerating compound (D).

By contrast, the resin compositions for acoustic matching of according to the present invention were acceptable in both pot life and low-temperature curing properties, and the acoustic matching sheets produced from the resin compositions for acoustic matching of according to the present invention were excellent also in breaking energy (Examples 1 to 34). These results are probably due to the following reasons; in each of the resin compositions for acoustic matching of Examples 1 to 34, the reaction time after the start of curing reaction, rather than the time from when the composition was prepared until curing reaction started, was reduced by the curing accelerator.

While the present invention has been described in connection with embodiments thereof, we do not intend to limit our invention in any detail of the description unless otherwise specified. Rather, the invention should be broadly construed without departing from the spirit and scope of the invention as defined by the appended claims.

REFERENCE SIGNS LIST 1 acoustic lens
2 acoustic matching layer (acoustic matching sheet)
3 piezoelectric element layer
4 backing member
7 housing
9 cord
10 ultrasound search unit (probe)

What is claimed is:
1. An acoustic probe comprising an acoustic matching layer, a piezoelectric element layer, and a backing member disposed in this order from a distal end, wherein the acoustic matching layer comprises a cured product formed by curing a resin composition for an acoustic matching layer, comprising:
  metal particles (A);
  an epoxy resin (B);
  a polythiol compound (C); and
  a cure-accelerating compound (D),
  wherein the epoxy resin (B) includes at least one epoxy resin selected from the group consisting of bisphenol A epoxy resins, bisphenol F epoxy resins, and phenol novolac epoxy resins, and
  the polythiol compound (C) includes a compound having at least two partial structures represented by general formula (1) below or at least two partial structures represented by general formula (2) below:

wherein, in general formula (1), one of $R^1$ to $R^5$ represents a sulfanyl group, the other four each independently represent a hydrogen atom, an alkyl group having 1 to 10 carbon atoms, or an aryl group having 6 to 14 carbon atoms, m represents an integer of 0 to 2, when m is 2, two $R^1$ may be the same or different and two $R^5$ may be the same or different, and * represents a linking site in the polythiol compound (C), and
  in general formula (2), one of $R^6$ to $R^{10}$ represents a sulfanyl group, the other four each independently represent a hydrogen atom, an alkyl group having 1 to 10 carbon atoms, or an aryl group having 6 to 14 carbon atoms, n represents an integer of 0 to 2, when n is 2, two $R^6$ may be the same or different and two $R^{10}$ may be the same or different, and * represents a linking site in the polythiol compound (C).
2. The acoustic probe according to claim 1, wherein the polythiol compound (C) is a polythiol compound having at least two partial structures represented by general formula (3) below:

general formula (3)

where, in general formula (3), $R^{11}$ and $R^{12}$ each independently represent a hydrogen atom or an alkyl group having 1 to 10 carbon atoms, s represents an integer of 0 to 2, and * represents a linking site in the polythiol compound (C).

3. The acoustic probe according to claim 2, wherein in general formula (3), at least one of $R^{11}$ or $R^{12}$ represents an alkyl group having 1 to 10 carbon atoms.

4. The acoustic probe according to claim 1, wherein the polythiol compound (C) is at least one of 1,4-bis(3-mercaptobutyryloxy)butane, pentaerythritol tetrakis(3-mercaptobutyrate), 1,3,5-tris(3-mercaptobutyryloxyethyl)-1,3,5-triazine-2,4,6(1H,3H,5H)-trione, trimethylolpropane tris(3-mercaptobutyrate), ethylene glycol bis(3-mercaptopropionate), tetraethylene glycol bis(3-mercaptopropionate), trimethylolpropane tris(3-mercaptopropionate), pentaerythritol tetrakis(3-mercaptopropionate), dipentaerythritol hexakis(3-mercaptopropionate), or tris[(3-mercaptopropionyloxy)ethyl] isocyanurate.

5. The acoustic probe according to claim 1, wherein the polythiol compound (C) is at least one of 1,4-bis(3-mercaptobutyryloxy)butane, pentaerythritol tetrakis(3-mercaptobutyrate), 1,3,5-tris(3-mercaptobutyryloxyethyl)-1,3,5-triazine-2,4,6(1H,3H,5H)-trione, or trimethylolpropane tris(3-mercaptobutyrate).

6. The acoustic probe according to claim 1, wherein the metal particles (A) include a transition metal in groups 4 to 12 of the periodic table.

7. The acoustic probe according to claim 6, wherein the metal particles (A) include a transition metal in period 4 of the periodic table.

8. The acoustic probe according to claim 1, wherein, relative to 100 parts by mass of a content of the metal particles (A), a content of the epoxy resin (B) is 5 to 80 parts by mass, a content of the polythiol compound (C) is 3 to 50 parts by mass, and a content of the cure-accelerating compound (D) is 0.05 to 5 parts by mass.

9. The acoustic probe according to claim 1, wherein, the polythiol compound (C) has a molecular weight of 200 to 1,000.

10. An acoustic measuring apparatus comprising the acoustic probe according to claim 1.

11. The acoustic measuring apparatus according to claim 10, wherein the acoustic measuring apparatus is an ultrasound diagnostic apparatus.

12. A method for producing an acoustic probe, comprising steps of
providing a piezoelectric element on a backing member,
forming an acoustic matching layer on the piezoelectric element, said acoustic matching layer comprising a cured product formed by curing a resin composition for an acoustic matching layer, and
forming an acoustic lens on the acoustic matching layer,
wherein the resin composition for an acoustic matching layer, comprises:
metal particles (A);
an epoxy resin (B);
a polythiol compound (C); and
a cure-accelerating compound (D),
wherein the epoxy resin (B) includes at least one epoxy resin selected from the group consisting of bisphenol A epoxy resins, bisphenol F epoxy resins, and phenol novolac epoxy resins, and
the polythiol compound (C) includes a compound having at least two partial structures represented by general formula (1) below or at least two partial structures represented by general formula (2) below:

general formula (1)

general formula (2)

wherein, in general formula (1), one of $R^1$ to $R^5$ represents a sulfanyl group, the other four each independently represent a hydrogen atom, an alkyl group having 1 to 10 carbon atoms, or an aryl group having 6 to 14 carbon atoms, m represents an integer of 0 to 2, when m is 2, two $R^1$ may be the same or different and two $R^5$ may be the same or different, and * represents a linking site in the polythiol compound (C), and in general formula (2), one of $R^6$ to $R^{10}$ represents a sulfanyl group, the other four each independently represent a hydrogen atom, an alkyl group having 1 to 10 carbon atoms, or an aryl group having 6 to 14 carbon atoms, n represents an integer of 0 to 2, when n is 2, two $R^6$ may be the same or different and two $R^{10}$ may be the same or different, and * represents a linking site in the polythiol compound (C).

* * * * *